Figure 1:
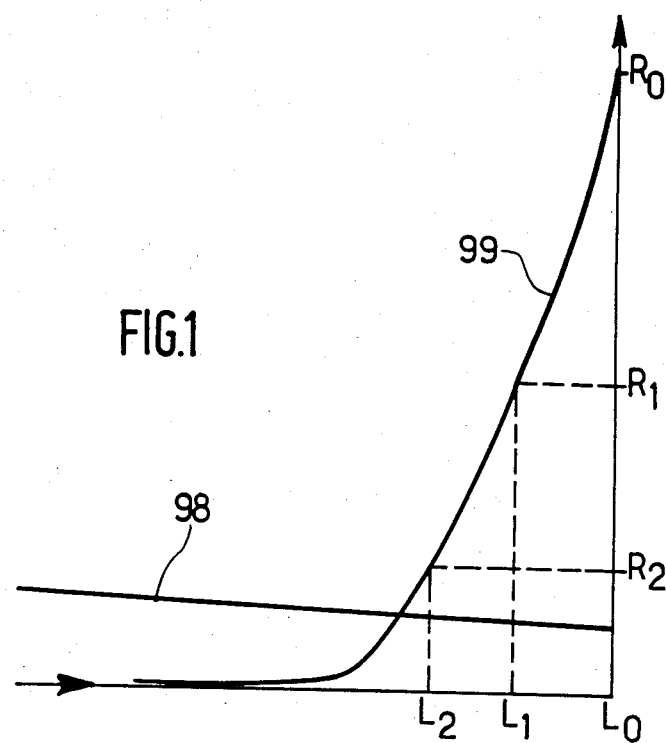

United States Patent [19]

Hazan et al.

[11] Patent Number: 4,639,137
[45] Date of Patent: Jan. 27, 1987

[54] METHOD OF AND DEVICE FOR DETERMINING WHEN A LIQUID-RENEWAL PROCESS IS TO BE TERMINATED

[75] Inventors: Jean-Pierre Hazan, Sucy-en-Brie; Michel Steers, Chennevieres-sur-Marne, both of France

[73] Assignee: U. S. Philips Corporation, New York, N.Y.

[21] Appl. No.: 691,597

[22] Filed: Jan. 15, 1985

[30] Foreign Application Priority Data

Jan. 23, 1984 [FR] France ................. 84 00980

[51] Int. Cl.$^4$ ............................. G01N 21/53
[52] U.S. Cl. ................... 356/339; 134/113; 250/574; 356/341; 356/343
[58] Field of Search ............ 356/339, 341, 343; 250/565, 574; 134/113

[56] References Cited

U.S. PATENT DOCUMENTS

| 3,200,700 | 8/1965 | Topol | 356/341 |
| 3,870,417 | 3/1975 | Bashank | 356/442 |
| 4,257,708 | 3/1981 | Fukuda | 356/442 X |

Primary Examiner—Davis L. Willis
Assistant Examiner—Matthew W. Koren
Attorney, Agent, or Firm—Rolf E. Schneider

[57] ABSTRACT

A method of renewing a used liquid for reuse of the same includes establishing a body of a reference liquid for comparison with renewed used liquid, and establishing a separate body of the used liquid adjacent the body of reference liquid. An incident light beam is produced for consecutive traversal of the body of used liquid and the body of reference liquid, the particles in the two liquid bodies thereby diffusing the light beam to provide respective luminous fluxes off the axis of the incident light beam. The two luminous light fluxes are separately detected and compared. This procedure is automatically terminated when the detected luminous light fluxes are substantially equal to each other.

7 Claims, 4 Drawing Figures

METHOD OF AND DEVICE FOR DETERMINING WHEN A LIQUID-RENEWAL PROCESS IS TO BE TERMINATED

This invention relates to a method of automatically controlling a liquid-renewal process in a liquid-renewal apparatus depending on the clarity of a renewed liquid through comparison with a reference liquid by means of a light emitter which produces light which, after it has traversed the reference liquid and the renewed liquid, is detected by light detectors which enable the clarity of the renewed liquid to be determined by electrical means and thereby enable the supply of renewal liquid to the liquid-renewal apparatus to be controlled.

It is obvious that the invention also relates to any device in which a liquid being renewed is brought into conformity with a reference liquid as in laundry or other washing machines and to equipment in which the quality of a liquid is controlled in relation to that of a reference liquid.

A method in accordance with the invention, which will be described in more detail by way of example, can be illustrated by a description of the cleaning operations, in particular the laundry rinsing operations, in a laundry washing machine. It is evident that any process of cleaning other materials using other liquids in conformity with the method falls within the scope of the present invention, which also applies to the use of a reference liquid other than tap water.

When laundry has been washed by means of a water-detergent solution, if required at a higher temperature than the ambient temperature, the washing water will contain contaminants, heavy and light detergent-particles, fabric particles etc. At the end of the washing operation this washing water is discharged and during the subsequent rinsing operation tap water is supplied in order to remove residual debris, contaminants and detergent-particles which have not been discharged at the end of the washing operation. This rinsing operation is effected either in consecutive water supply and discharge cycles or with a continuous water supply and discharge. The amount of tap water required for the rinsing operation depends on the load of laundry, its degree of soiling and the amount of detergent used. It is obvious that if a fixed rinsing time is used the amount of water may be too small or too large.

A customary method of determining when the rinsing operation is satisfactory and may be terminated is to visually examine the clarity of the effluent.

Such a method is described in British Pat. No. 1,401,426, which employs the optical properties of a pure rinsing liquid to determine the optimum instant at which the rinsing operation should be terminated.

Said method utilizes a light source which emits light in two opposite directions, which light passes through two measuring cells which each have an associated light detector, one of the cells receiving rinsing water to be checked and the other receiving pure tap water directly from the water main. Since the two detectors are identical, the luminous flux issuing from the cell containing the rinsing water may be compared with that from the cell containing the pure tap water by electrical means.

However, this method has one disadvantage. The two measuring cells, i.e. the cell containing the effluent rinsing water and the cell containing the pure tap water are spaced from each other and receive separate light beams issuing from the light source. As the rinsing water is a liquid whose degree of soiling varies from a state of substantial soiling to a desired state of high purity, it will be evident that during use of the washing machine the transparent walls through which the light beams pass are gradually soiled and become opaque. However, the walls of the cell containing the pure tap water, are not or are hardly affected by this process.

As a result, the optical measurements, which are based on the measurement of the luminous flux transmitted by the cell containing the rinsing water, will gradually become representative of the degree of soiling of the cell walls rather than that of the rinsing water; therefore said walls have to be cleaned very frequently, which is undesirable.

The present invention aims at minimizing the soiling of the walls of the cell containing the liquid to be analysed, so that cleaning said walls is not necessary.

In accordance with the invention a method of the present type is characterized in that:

a light beam is incident in such a way that it first traverses a cell containing the renewed liquid before it reaches the cell containing the reference liquid;

the luminous flux diffused by the particles in each of the two liquids is detected separately, off the axis of the incident light beam;

the luminous fluxes received simultaneously during said detections are compared;

the liquid-renewal process is terminated automatically when the received fluxes are substantially equal to each other.

Thus, the light which has first passed through the renewed liquid and the walls of the cell containing said liquid before it passes through the cell containing the reference liquid is attenuated owing to the soiling of the walls of the cell containing the renewed liquid, which attenuation is thus taken into account in determining the degree of clarity of the renewed liquid. The flux which reaches the reference cell is not the same as the luminous flux emitted by the light source but has been attenuated as a result of its passage through the cell containing the renewed liquid. In this way the luminous flux which reaches the reference cell varies with the degree of soiling of the transparent walls of the cell containing the renewed liquid, in such a way that said soiling does not affect the final measurement results obtained by means of the two light detectors, which thus provide a real measure of the degree of clarity of the renewed liquid in comparison with that of the reference liquid. Indeed, before it reaches the light detectors, the light beam emitted by the light source passes through an equal number of walls which may become opaque.

The two light detectors are connected to electrical means enabling the luminous fluxes received by the two light detectors to be compared with each other. In a method applied to the rinsing operations in a cleaning apparatus, for example a laundry or other washing machine, the quality of the effluent rinsing water should be as close as possible to that of the water in the reference cell. Thus, comparison is effected until the two cells receive substantially the same luminous flux. The reference liquid is then pure water and the renewed liquid is the effluent rinsing water.

Alternatively, the method may be used for bringing soiled water into conformity with clean water in a water purifying process.

Figure 3:
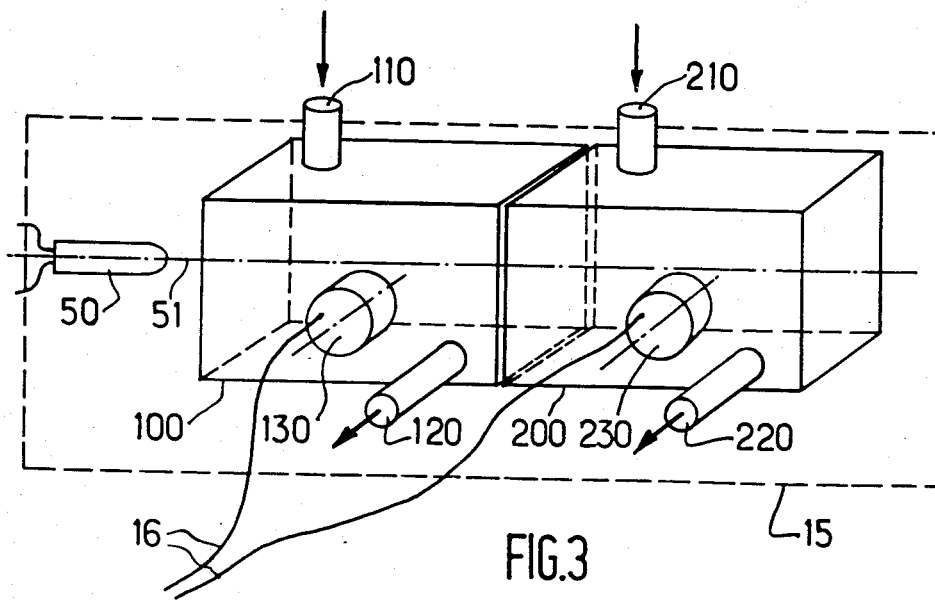
Figure 2:
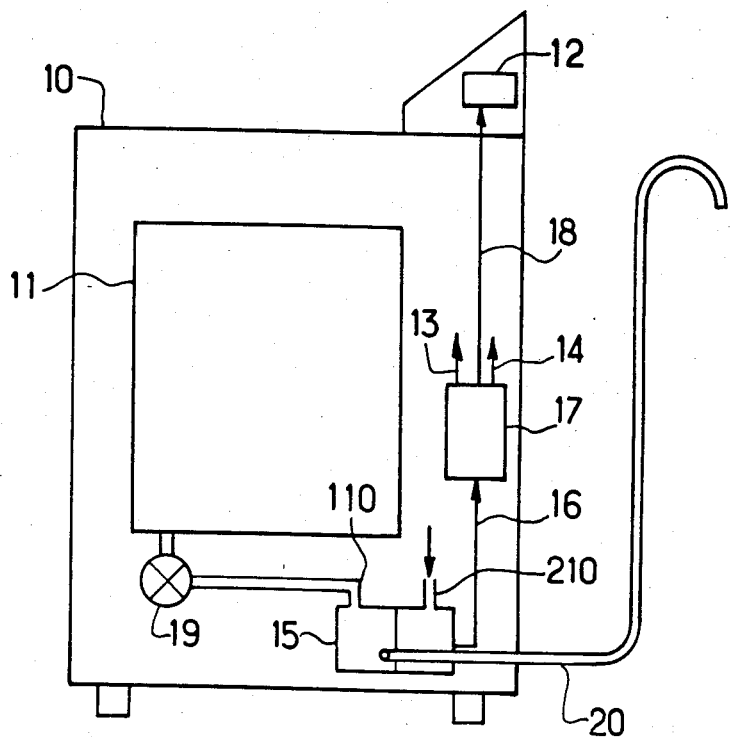
Figure 4:
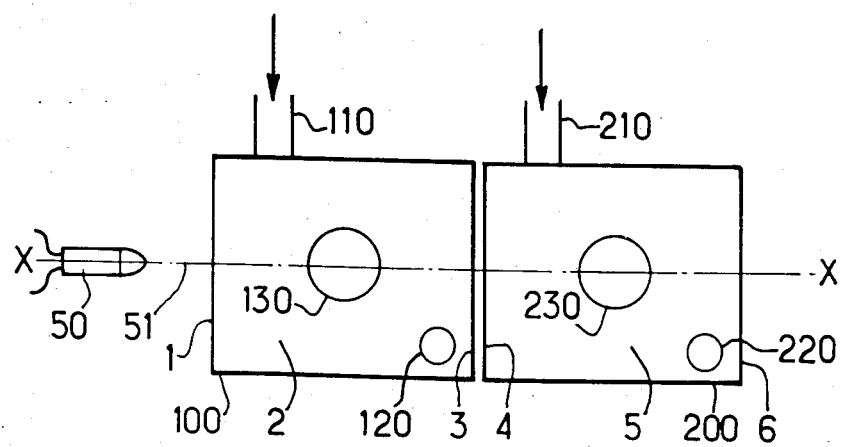

The invention will now be described in more detail with reference to the accompanying drawings, in which FIG. 1 represents the variation in the resistance of a photo resistor as a function of the incident luminous flux which depends on the degree of clarity of a liquid, FIG. 2 shows schematically a laundry washing machine comprising a device in accordance with the invention for measuring the degree of clarity of the effluent rinsing water, FIG. 3 is a perspective view of the device for measuring the degree of clarity of the water, and FIG. 4 is a side view of this device.

FIG. 1 shows two curves 98, 99 which represent the variation of the resistance of a photo resistor as a function of the degree of clarity of a liquid in the case of transmission (curve 98) and diffusion (curve 99), respectively. The variation of the resistance value of the photo resistor is inversely proportional to the luminous flux received by this photo resistor. For the sake of clarity the curve 98 is represented on an enlarged scale in comparison with the curve 99.

The degree of clarity $L_0$ corresponds to water of a very high degree of clarity, i.e. the transmitted luminous flux detected by a photo resistor is maximum and the diffused flux is very small. As the clarity diminishes this results in, for example, water with a clarity $L_1$, and finally normal tap water with a clarity $L_2$. The resistance of the photo resistor which receives the diffused luminous flux varies more rapidly than the resistance of the photo resistor which receives the transmitted luminous flux. Consequently, a measurement of the diffused luminous flux is more sensitive.

FIG. 2 shows only those elements which are necessary to understand how a device for measuring the clarity of water can be used in a laundry washing machine 10. Downstream of the draining pump 19 in the conduit which leads from the tub 11 to the drain 20, water used for rinsing is branched off by means of a supply conduit 110. This water is supplied to the clarity measuring device 15, which also receives reference water, in the present example tap water, via the supply conduit 210. The measuring device 15 supplies two electric signals 16 to a comparator device 17 which, when the input signals are equal, supplies an output signal 18 which actuates the programming device 12 and generates signals 13, 14 which warn the user in the case of failure of the device. Thus, the cycle of operations of the laundry washing machine 10 is controlled by the comparator output signal 18.

FIG. 3 shows in more detail the device 15 for measuring the clarity of water. It comprises a light source 50 emitting along the line X—X a light beam 51 which is incident on a renewed-liquid cell 100 which is provided with the supply conduit 110 and a discharge conduit 120 for the rinsing water. A luminous-flux detector 130 which is arranged substantially perpendicularly to the direction of propagation of the light beam 51 receives the light which has been diffused by the particles in the renewed liquid. Viewed in the direction of propagation of the incident light beam 51 the renewed-liquid cell 100 in the device 15 is followed by a reference-liquid cell 200, which in the present case contains tap water, and which is provided with the supply conduit 210 and a discharge conduit 220. A luminous-flux detector 230, which is identical to the preceding detector and which is arranged substantially perpendicularly to the direction propagation of the incident light beam 51, receives the light which has been dispersed by the particles in the reference liquid. The detectors 130, 230 supply electric signals 16 which are processed in the comparator device 17 (FIG. 2).

In addition to the elements already described FIG. 4 shows:

for the renewed-liquid cell 100:
(a) the input surface 1 receiving the incident light beam 51;
(b) the detection surface 2 through which the flux produced by the incident light beam 51 passes and which has been diffused by the particles in the renewed liquid;
(c) the output surface 3 through which the luminous flux resulting from the incident light beam 51 passes.

for the reference cell 200:
(a) the input surface 4 receiving the luminous flux which has traversed the renewed-liquid cell 200;
(b) the detection surface 5 through which a luminous flux passes, which flux is produced by the light beam which has traversed the reference cell 200 and which has been diffused by the particles in the reference liquid.

The surfaces 1, 2, 3, 4, 5 are highly transparent over part or all of their surface areas, so that the light of the incident beam 51 can reach the renewed-liquid and the reference liquid and subsequently the detectors 130, 230.

The surfaces 1, 2, 3 become opaque to the same extent. The measurements carried out by means of the detectors 130, 230 allow for light which has passed through the surfaces 1, 2 and the surfaces 1, 3 respectively. The opacity of the walls of the cell 100 will influence the two measurements to the same extent.

The surfaces 1, 3, 4 extend substantially perpendicularly to the direction of the incident beam 51 in order to transmit the maximum flux. The surfaces 2, 5 extend substantially parallel to the direction of the incident beam 51. However, an axial offset relative to these positions is still in conformity with the invention. It is required only that the luminous flux reaching the detectors 130, 230 is adequate. Similarly, if the surfaces 1, 2, 3, 4, 5 are not plane to improve the directivity of the light beams, this is also in conformity with the invention.

The renewed-liquid cell 100 and the reference-liquid cell 200 may be formed by dividing a larger cell by means of a partition. The output surface 3 of the cell 100 and the input surface 4 of the reference cell 200 then constitute the two surfaces of said partition.

Similarly, the cells 100, 200 may be identical and juxtaposed. Thus, a space may be formed between the surfaces 3 and 4, which is of no consequence if it does not affect the transmission of light between the surfaces 3 and 4.

Surfaces other than the surfaces 1, 2, 3, 4, 5 need not be transparent to light, which means that if they are transparent to light which may disturb the measurements the assembly of cells should be provided with a protective sleeve or coating which ensures that spurious light cannot disturb the measurements. Only the light issuing from the light source 50 should be taken into account for a correct operation of the device.

Moreover, a suitable collimation may be applied at the location of the light detectors in order to ensure that they do not receive a part of the luminous flux which has been transmitted directly from the light source 50 to the output surface 3, and which would be reflected to the detector 30 by said surface. The same applies to the output surface 6 and the detector 230.

In the case of a washing machine the device is designed to compensate for the slow and gradual soiling of the walls over a very wide range. In extreme cases in which the opacity becomes excessive the cell containing the renewed liquid is replaced. Owing to the modular construction of the device only the cell containing the renewed liquid can be replaced.

The electrical means is designed to allow for extreme situations which may occur in operation. The light detectors 130, 230 may be constructed by means of, for example, photo resistors. FIG. 1 shows the variation in the resistance of each photo resistor as a function of the incident luminous flux, i.e. of the degree of clarity of the water. Two curves are shown:

curve 98 which corresponds to transmission measurements for which the variation in resistance of the photo resistor indicates that the sensitivity as a function of the degree of clarity of the water is comparatively low;

curve 99 which corresponds to diffusion measurements for which the variation in the resistance of the photo resistor indicates that the sensitivity as a function of the degree of clarity of the water is high.

The invention mainly utilizes said curve 99 which corresponds to diffusion measurements. However, depending on the location of the particle which gives rise to light diffusion and depending on the angle of the detector axis with the axis of the incident light beam 51, the measurements may involve both diffusion parameters and transmission parameters. However, the diffusion parameters are more favourable for the operation of the device.

If there is no luminous flux the photo resistor has a dark resistance $R_0$. When the walls 1 and 3 have become opaque during use of the device, the amount of light reaching the reference cell will decrease gradually. It is necessary to ensure that the light flux reaching said cell remains above a threshold level below which a replacement of the renewed-liquid cell is necessary. This threshold may for example correspond to a resistance value $R_1$ of the photo resistor. Since this resistance value is inversely proportional to the incident luminous flux, it should remain below the value $R_1$. This value is for example $R_1 = R_0/2$. It may be adapted to suit a specific use.

The quality tap of the water may vary locally. Indeed, the tap water may contain iron or other extraneous substances: debris from conduits, and other particles which affect its clarity. When the renewed-liquid cell is empty and the reference cell is filled with tap water, the photo resistor of the light detector 230 will have a resistance value $R_{230} = R_2$ which is typical of the quality of the water at the location where the device is used. This value is for example $R_2 = R_0/5$.

Each time that the washing machine is put into operation, the comparator device 17 tests the operation of the device for measuring the clarity of the water. The comparator device 17 converts the resistance values $R_0$, $R_1$, $R_2$, $R_{230}$, $R_{130}$ into corresponding voltage levels $V_{R0}$, $V_{R1}$, $V_{R2}$, $V_{R230}$, $V_{R130}$ which are compared with each other.

When the light source 50 is switched on, this comparison is made after the reference cell has been filled with tap water, the renewed-liquid cell remaining empty. Thus, the light detector 130 measures the dark resistance $R_0$. The following three situations may then occur:

When the comparator device 17 indicates that $V_{R230} = V_{R130} = V_{R0}$ it follows that the light source 50 is defective and a light-source-failure signal 14 warns the user of a defect.

When the comparator device 17 indicates that the signal $V_{R230}$ lies between the reference values $V_{R0}$ and $V_{R1}$ the luminous flux is insufficient, which means that the walls have become opaque. The signal 13 then provides an indication to the user that the walls have become opaque.

When the comparator device 17 indicates that the signal $V_{R230}$ is smaller than $V_{R1}$ the device 15 for measuring the clarity is in its normal operating condition and the rinsing process may begin. All these signals actuate indicators which provide a visible or audible warning to the user.

It is obvious that the values of the voltages $V_{R0}$, $V_{R1}$, $V_{R2}$ are subject to certain tolerances which can be determined by those skilled in the art.

What is claimed is:

1. A method of renewing a used liquid for reuse of the same, which includes establishing a body of a reference liquid for comparison with renewed used liquid; establishing a separate body of the used liquid adjacent the body of reference liquid; producing an incident light beam for consecutive traversal of the body of used liquid and the body of reference liquid, the particles in the two liquid bodies thereby diffusing the light beam to provide respective luminous fluxes off the axis of said incident light beam; separately detecting said two luminous light fluxes and comparing the same; and automatically terminating such procedure when the detected luminous light fluxes are substantially equal to each other.

2. A method according to claim 1, in which the respective luminous fluxes are substantially perpendicular to the axis of the incident light beam.

3. Apparatus for renewing a used liquid for reuse of the same, which includes a first impermeable cell for the used liquid; a second impermeable cell for a reference liquid for comparison with renewed used liquid, said two cells being adjacent each other; means to produce an incident light beam for consecutive traversal of the first cell and the second cell, the particles in the liquids in the respective cells thereby diffusing the light beam to provide respective luminous fluxes off the axis of said incident light beam; two light detectors for respectively receiving only said two luminous fluxes, the respective cells being opaque to light from any spurious light source; and means to automatically terminate the comparison procedure when the detected luminous fluxes are substantially equal to each other.

4. Apparatus according to claim 3, in which the two light detectors are arranged substantially perpendicularly to the axis of the incident light beam.

5. Apparatus according to claim 3, in which the two adjacent cells are separated by a single wall.

6. Apparatus according to claim 3, in which the two adjacent cells are separated by two walls, the medium between the two walls having no significant influence on the optical properties to be determined.

7. Apparatus according to claim 6, in which the two adjacent cells constitute a modular arrangement of two identical cells.

* * * * *